United States Patent
Won

(10) Patent No.: US 10,772,728 B2
(45) Date of Patent: Sep. 15, 2020

(54) IMPLANTS AND METHODS FOR COSMETIC SURGERY

(71) Applicants: Yougun Won, Daejeon (KR);
BIOCOEN CO., LTD., Yongin-si, Gyeonggi-do (KR)

(72) Inventor: Yougun Won, Brookline, MA (US)

(73) Assignees: Yougun Kim, Daejeon (KR);
BOICOEN CO., LTD., Yongin-si, Gyeonggi-Do (KR)

( * ) Notice: Subject to any disclaimer, the term of this patent is extended or adjusted under 35 U.S.C. 154(b) by 282 days.

(21) Appl. No.: 15/415,818

(22) Filed: Jan. 25, 2017

(65) Prior Publication Data
US 2018/0028302 A1 Feb. 1, 2018

(30) Foreign Application Priority Data

Jul. 26, 2016 (KR) .......................... 10-2016-0094758

(51) Int. Cl.
| | |
|---|---|
| A61F 2/28 | (2006.01) |
| A61B 17/56 | (2006.01) |
| A61B 17/80 | (2006.01) |
| A61F 2/30 | (2006.01) |

(52) U.S. Cl.
CPC .............. *A61F 2/28* (2013.01); *A61B 17/56* (2013.01); *A61B 17/8085* (2013.01); *A61F 2/30942* (2013.01); *A61B 17/80* (2013.01); *A61B 2017/564* (2013.01); *A61F 2220/0008* (2013.01); *A61F 2240/002* (2013.01)

(58) Field of Classification Search
CPC ....... A61F 2/28; A61F 2/30731; A61F 2/0059
See application file for complete search history.

(56) References Cited

U.S. PATENT DOCUMENTS

| | | | |
|---|---|---|---|
| 5,089,017 A | 2/1992 | Young et al. | |
| 2007/0129809 A1* | 6/2007 | Meridew ............. | A61F 2/30721 623/22.32 |
| 2008/0108989 A1 | 5/2008 | Parsell et al. | |
| 2008/0140200 A1 | 6/2008 | Heinz | |
| 2009/0259263 A1 | 10/2009 | Steger et al. | |
| 2015/0051650 A1 | 2/2015 | Verstreken et al. | |

FOREIGN PATENT DOCUMENTS

| | | |
|---|---|---|
| JP | 10-014956 A | 1/1998 |
| KR | 2010-0008951 U | 9/2010 |
| KR | 2012-0125409 A | 11/2012 |

OTHER PUBLICATIONS

Invitation to Pay Additional Fees for International Application No. PCT/US2017/014996, dated Mar. 24, 2017.
International Search Report and Written Opinion for International Application No. PCT/US2017/014996, dated Jun. 9, 2017.

* cited by examiner

*Primary Examiner* — Marcia L Watkins
(74) *Attorney, Agent, or Firm* — Novick, Kim & Lee, PLLC; Jae Youn Kim; Jihun Kim

(57) ABSTRACT

An implant for attachment to a human pelvic bone for cosmetic purposes. The implant is attachable to the iliac crest. A silicone cover is attachable to the implant. Implant plates may be attached to the humeral bone, the tibia, and the femur, and silicone may be attached to the plates.

17 Claims, 16 Drawing Sheets

IMPLANTS AND METHODS FOR COSMETIC SURGERY

CROSS-REFERENCE TO RELATED APPLICATIONS

This application claims priority to and the benefit of Korean Patent Application No. 10-2016-0094758, filed on Jul. 26, 2016, the disclosure of which is incorporated herein by reference in its entirety.

FIELD

The present invention relates to implants for cosmetic surgery, and methods of implant attachment.

DISCUSSION OF RELATED ART

Beauty goals pursued by many people include overall appearances including their body figures. The size and shapes of various body parts can play a role in attractiveness. More particularly, some studies have found that certain proportions of a person's waist width to pelvis width are deemed attractive, regardless of absolute lateral width. The waist-to-hip ratio is obtained by dividing a lateral width of the waist by a lateral width of the pelvis. Some studies have found that a waist-to-hip ratio of approximately 0.6-0.7 may be deemed attractive.

To achieve such waist-to-hip ratios, chemical agents, liposuction, or the like have been performed to reduce a lateral width of a waist. However, due to basic sizes of internal organs and a size of the skeleton, there are limitations to reducing a lateral width of a waist and it is difficult to deform an innate size.

Also, there have been attempts to increase a lateral width of a thigh, rather than a pelvis, by transplanting autologous fat or a silicon implant onto soft tissue such as subcutaneous tissue, adipose tissue, or the like. However, such attempts have not always worked due to stressful forces on soft tissues which does not provide firm fixation. Tight clothing and shearing force during ambulation can eventually lead the implant or grafted material deformed or displaced.

Attempts have been made on soft tissue to increase a lateral width of a pelvis, but these approaches have encountered problems.

BRIEF SUMMARY

Embodiments of the present disclosure provide an implant for cosmetic surgery on a pelvic bone or other human bones. The implant may be stably fixed to an iliac crest of a pelvis to increase an apparent lateral width of the pelvis.

According to one embodiment, there is provided a method of increasing an apparent lateral width of a human pelvis. The method includes contacting a bio-compatible implant to an iliac crest of a recipient. The method further includes inserting one or more bone fasteners into the iliac crest to fix the implant to the iliac crest in a position in which the implant extends laterally beyond an outermost lateral region of the iliac crest.

According to another embodiment, a method of manufacturing an implant for cosmetic surgery on a pelvic bone includes imaging an iliac crest of a particular recipient. The method further includes forming an implant having a contact surface and an outer surface, wherein the contact surface has a shape that matches a shape of an outer surface portion of the iliac crest, the outer surface portion of the iliac crest being the portion that the contact surface of the implant contacts when fixed to the iliac crest, and wherein the outer surface of the implant is configured to extend beyond an outermost lateral region of the iliac crest.

According to a further embodiment, a bio-compatible implant is provided. The implant is for cosmetic surgery on a pelvic bone to increase an apparent lateral width of a pelvis of a recipient. The implant includes an outer surface which extends laterally beyond a an outermost lateral region of an iliac crest when the implant is fixed to an iliac crest of a recipient. The implant also includes a contact surface configured to contact an outer surface contact area of an iliac crest of a recipient.

According to yet another embodiment, there is provided a bio-compatible implant for cosmetic surgery on a pelvic bone to increase an apparent lateral width of a pelvis of a recipient. The implant includes a base portion to be fixed relative to an iliac crest of the pelvis, the base portion having an exterior surface. The implant also includes a separation preventer extending from the base portion, wherein the separation preventer is shaped to wrap around at least a portion of the iliac crest the base portion is positioned over the iliac crest.

According to another embodiment, a method of changing an apparent shape of a human body part using an implant is provided. The method includes attaching a plate to a human bone, and attaching an implant to the plate, the implant comprising a pliable material.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION

Figure 1:
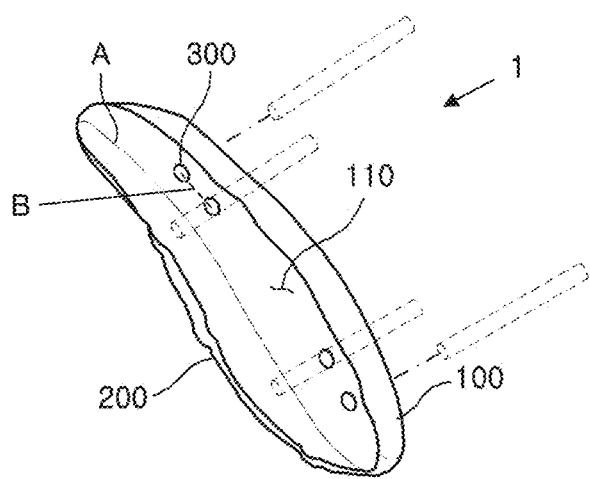
FIG. 1 shows an implant for cosmetic surgery on a pelvic bone according to a first embodiment of the present disclosure.
Figure 2:
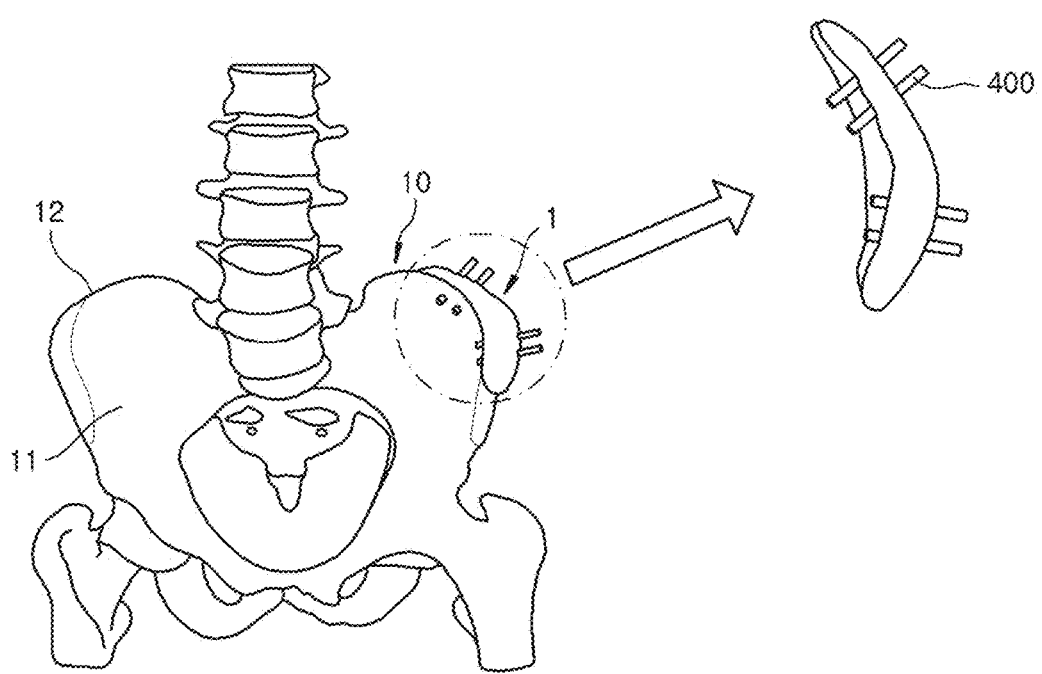
FIG. 2 shows the implant of FIG. 1 fixed to a pelvis of a human body, and an enlarged view of the implant prior to fixation.
Figure 3:
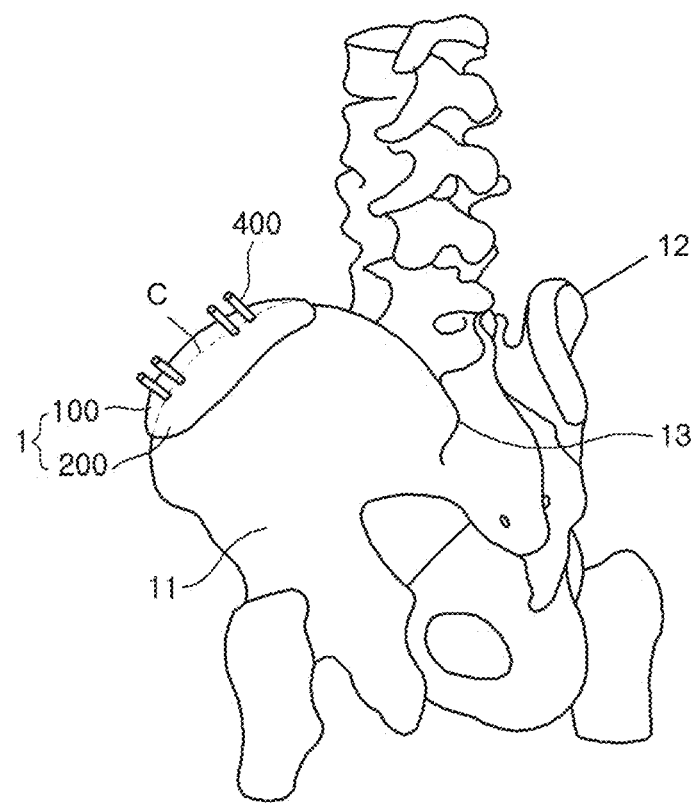
FIG. 3 is a side view of the implant of FIG. 2.
Figure 4:
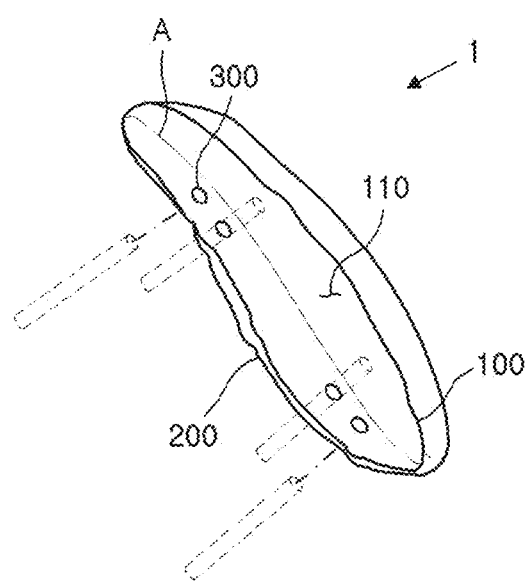
FIG. 4 shows a modified version of the implant of FIG. 1.
Figure 5:
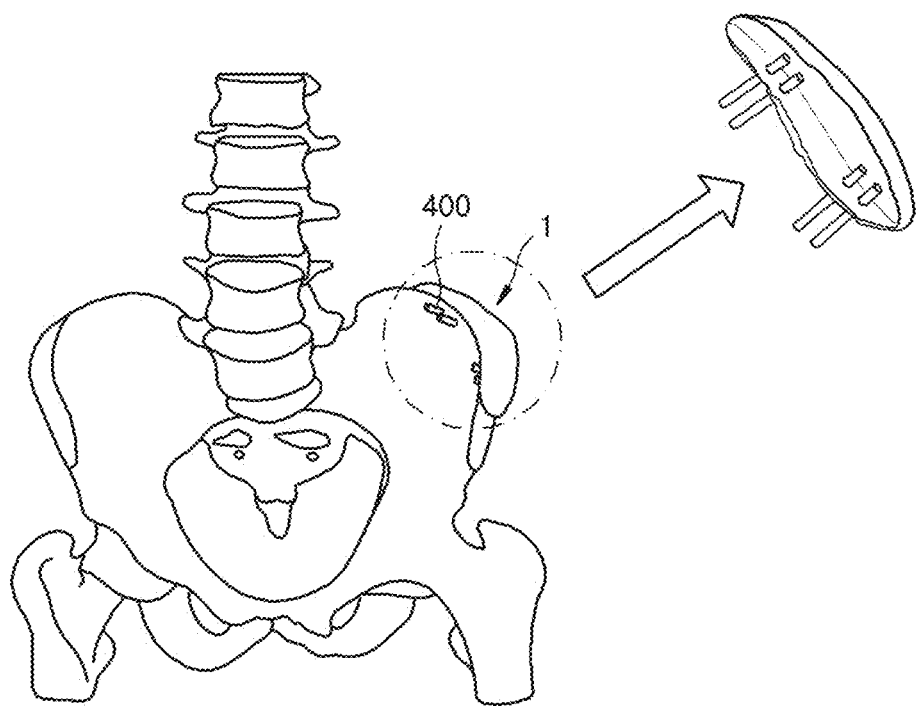
FIG. 5 shows the implant of FIG. 4 fixed to a pelvis of a human body, and an enlarged view of the implant prior to fixation.
Figure 6:
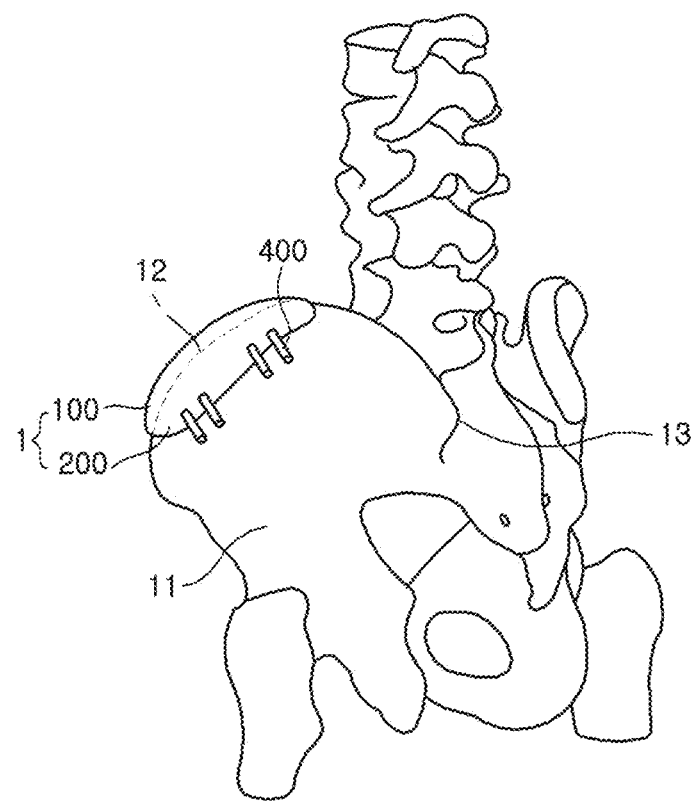
FIG. 6 is a side view of the implant of FIG. 5.
Figure 7:
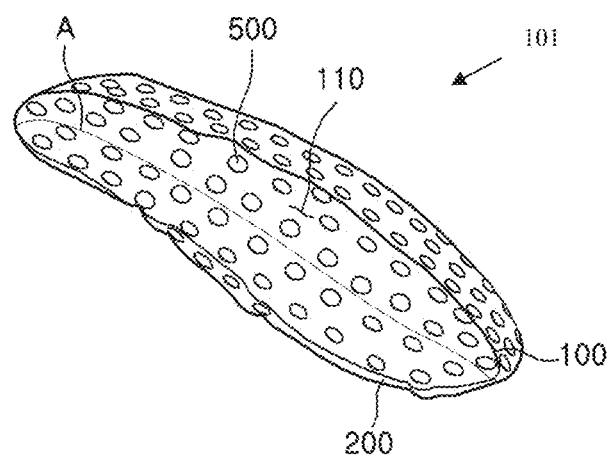
FIG. 7 shows an implant for cosmetic surgery on a pelvic bone according to a second embodiment.

It should be understood that aspects of the invention are described herein with reference to certain illustrative embodiments and the figures. The illustrative embodiments described herein are not necessarily intended to show all aspects of the invention, but rather are used to describe a few illustrative embodiments. Thus, aspects of the invention are not intended to be construed narrowly in view of the illustrative embodiments. In addition, it should be understood that aspects of the invention may be used alone or in any suitable combination with other aspects of the invention. Throughout the description, a detailed description of well-known components or functions may be omitted for clarity purposes.

Because the present invention may be variously modified and may include several embodiments, particular embodiments will be shown in the drawings and described in detail. However, it should be understood that the present invention is not limited to the particular embodiments and includes all modifications, equivalents, and substitutes included in the concept and technical scope of the present invention.

Implant

Embodiments disclosed herein relate to implants that are attachable to a human bone to alter the external appearance of the body part. In some embodiments, the implant comprises a metal implant attached to a bone. In some embodiments, a pliable material is attached to the metal implant that is attached to the bone.

An implant 1 for cosmetic surgery on a pelvic bone according to a first embodiment is described with reference to FIGS. 1 to 6. The implant 1 may include a base portion 100 and a separation preventer 200. The implant 1 may be fixed to one side of a pelvis 10 of a recipient, e.g., on an iliac crest 12. With such an arrangement, a lateral width of the pelvis 10 may be increased by as much as a thickness of the implant 1. A similar implant may be attached to the recipient's opposite iliac crest for symmetry.

The base portion 100 may be fixed to the iliac crest 12 in some embodiments. The iliac crest 12 refers to an edge that forms an upper end of an ilium 11, as is known to those of skill in the art. The base portion 100 may include a contact surface 110 that comes into contact with the iliac crest 12. The contact surface 110 may have a shape which substantially corresponds to the shape of the portion of the iliac crest 12 which the contact surface contacts. In some embodiments, the contact surface 110 is manufactured (e.g., molded) to match a shape of the iliac crest 12 of a particular recipient.

A separation preventer 200 may be provided to contact at least part of the iliac crest 12 when the base portion 100 is fixed to the iliac crest 12. The separation preventer 200 may extend from the base portion 100, and may be curved such that it can grasp an iliac crest by wrapping around a portion of the iliac crest. The separation preventer 200 may extend in at an abrupt angle from an edge of the contact surface 110 of the base portion 100, or the separation preventer 200 may extend at a gradually changing angle. In the embodiment shown in FIG. 1, a line A marks the border of the separation preventer 200 and the base portion 100 along an interior surface of the implant. The separation preventer 200 may extend from one portion of the edge of the contact surface 110, may extend from two or more portions thereof, or may extend from the entire perimeter edge of the contact surface 110. In some embodiments, no clear demarcation exists between the base portion and the separation preventer. Instead, a transition zone may exist where the base portion transitions throughout a small area to the separation preventer.

The base portion 100 and the separation preventer 200 are formed of a titanium alloy in some embodiments. The base portion 100 and the separation preventer 200 may be formed of a stainless steel alloy, polyethylene, a bio-ceramic, or any other suitable bio-compatible material. In some embodiments, the base portion 100 and the separation preventer 200 are formed of polyetheretherketone (PEEK), polymethyl methacrylate (PMMA), or other similar materials. The base portion 100 may be formed of a different material than the separation preventer 200 in some embodiments. Further, the base portion and/or the separation preventer may be formed of more than one material.

Titanium alloy, Stainless steel alloy, polyethylene, and bio-ceramic have outstanding bio-stability and bio-compatibility characteristics due at least in part to being nontoxic and having elasticity and strength similar to human bones. Accordingly, when the implant 1 is formed of such materials, side effects such as a foreign body reaction or infection may be reduced. In some embodiments, a bio-compatible implant may include some materials that are not bio-compatible, but these materials may be enclosed within bio-compatible materials.

As described above, the implant 1 may come into close contact with the iliac crest 12 (e.g., via the contact surface 110) and be fixed to the iliac crest 12 with the separation preventer 200. However, because the pelvis 10 is a part of a human body that frequently moves or receives a relatively large amount of external forces including shocks, bone fasteners, such as bone screws, may be used to further stabilize the implant to the iliac crest 12.

In some embodiments, one or more bone screws 400 may be placed through one or more fastener holes 300 in the base portion 100 and/or the separation preventer 200. The fastener holes 300 may be oriented such that each of the bone screws 400 passes through the fastener holes 300 in a direction perpendicular to the contact surface 110 and/or the surface of the iliac crest 12 at the bone screw location. However, the direction in which the bone screws 400 are inserted into the iliac crest 12 is not limited thereto, and the bone screws may extend through the contact surface 110 and into the iliac crest 12 at any suitable angle.

As one example, at least one pair of fastener holes 300 may be formed in the contact surface 110 of the base portion 100. Here, the at least one pair of fastener holes 300 may be formed to be arranged on a virtual line B which is substantially parallel to line A; line A being the transition from the base portion 100 to the separation preventer 200. One or more bone screws may be provided to pass through the fastener holes and into the iliac crest. Each of the screws may have the same length as one another, or they may have different lengths from one another.

For example, because the iliac crest 12 has a curvature that increases as it progresses downwardly, the bone screws 400 that pass through the fastener holes 300 may have different lengths. More particularly, one or more shorter bone screws may be used with the fastener holes 300 that are positioned to correspond to a top of the iliac crest 12, and one or more longer bone screws may be used with the fastener holes that are positioned to correspond to a bottom of the iliac crest 12. In some embodiments, the lengths of the shorter and longer bone screws may be 2.7 mm and 3.5 mm respectively.

In some embodiments, fastener holes may be formed in the separation preventer 200. In such an embodiment, one or more of the bone screws may pass through the fastener holes in a direction perpendicular to an inner surface of the separation preventer 200 and inserted into the iliac crest 12. The one or more fastener holes may be arranged in a virtual line C parallel to line A. However, the direction in which the bone screws 400 are inserted into the iliac crest 12 is not limited thereto, and the bone screws may be inserted into the iliac crest 12 in various directions.

In the illustrated embodiment, because the bone screw 400 passes through in the direction perpendicular to the inner surface of the separation preventer 200, it is unnecessary to consider the curvature of the iliac crest 12 when determining the length of the bone screw 400. Accordingly, when the plurality of bone screws 400 are provided, the plurality of bone screws 400 may have the same length in some embodiments.

The fastener holes may be of any suitable shape. In some embodiments, the fastener holes are circular. In other embodiments, the fastener holes are elongated slots with rounded ends. Fastener holes of different shapes may be used in the same implant. In still further embodiments, implants may include indentations or guides on an implant, and a bone screw may be drilled through the implant at those locations to form a hole.

By using the separation preventer 200 and the bone screws 400, the insert 1 can be securely fixed to the iliac crest 12 so as to resist external forces.

Figure 8:
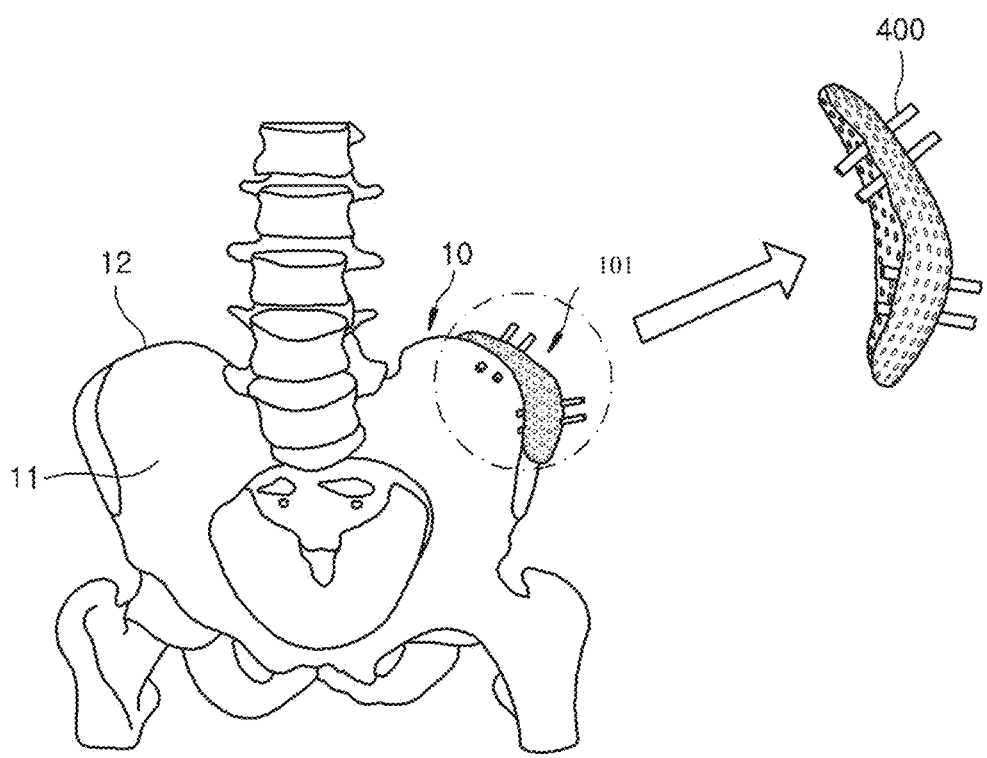
FIG. 8 shows the implant of FIG. 7 fixed to a pelvis of a human body, and an enlarged view of the implant prior to fixation.
Figure 9:
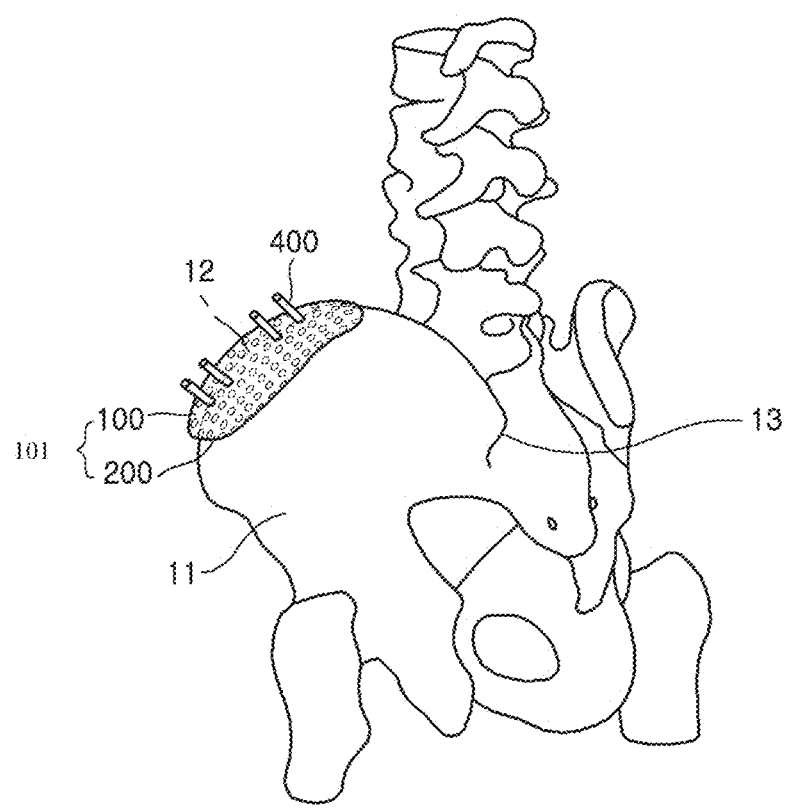
FIG. 9 is a side view of the implant of FIG. 8.
Figure 10:
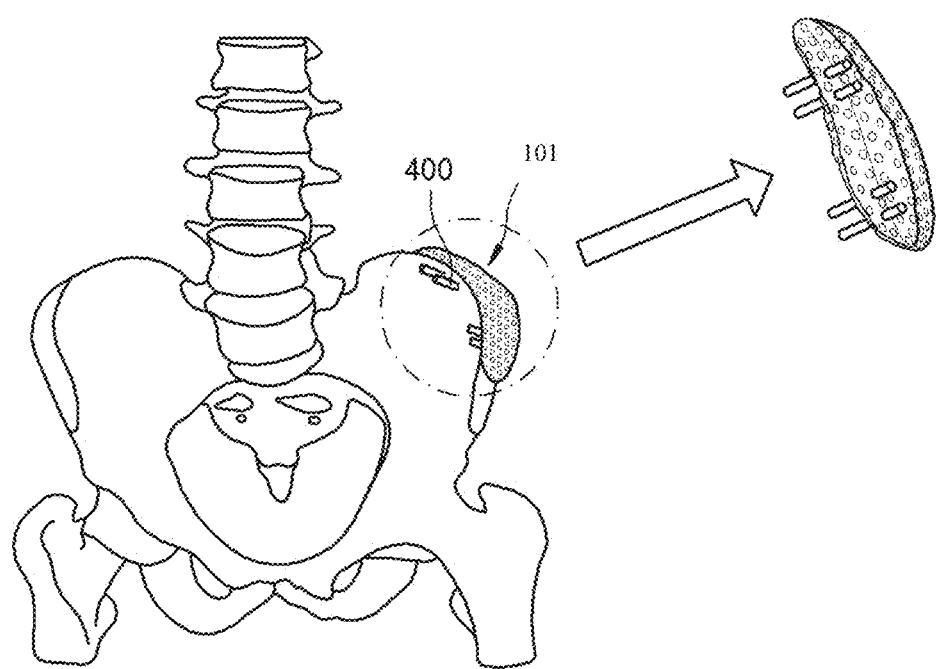
FIG. 10 shows a modified version of the implant of FIG. 7.
Figure 11:
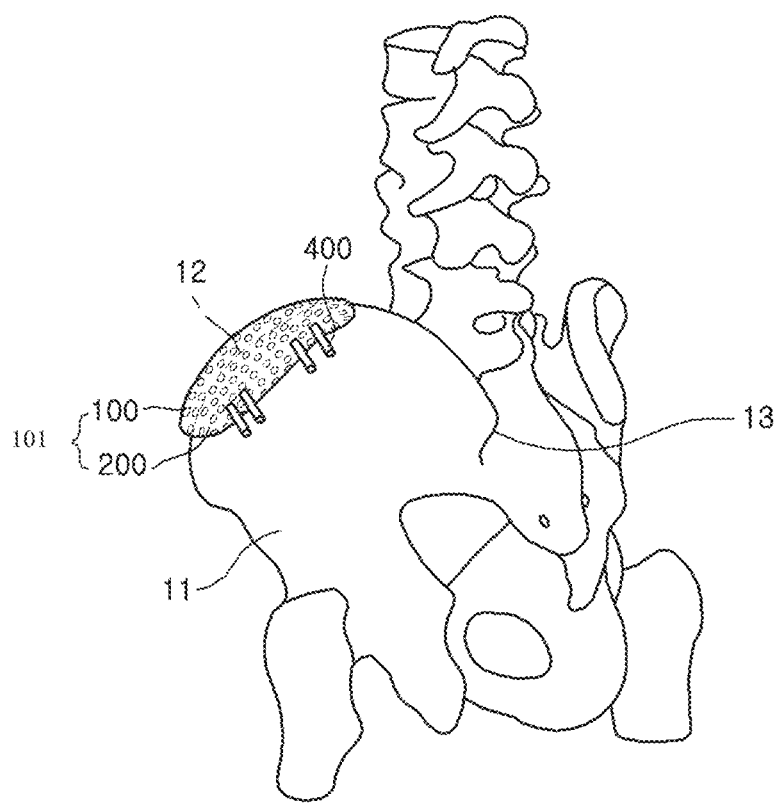
FIG. 11 is a side view of the implant of FIG. 10.

A second embodiment of an implant 101 for cosmetic surgery on a pelvis is shown in FIGS. 7 to 11. FIG. 8 shows the implant of FIG. 7 fixed to a pelvis of a human body. FIG. 9 is a side view of the implant of FIG. 8. FIG. 10 shows a modified version of the implant of FIG. 7. FIG. 11 is a side view of the implant of FIG. 10.

Implant 101 is similar to implant 1 of the first embodiment, but additionally includes a plurality of through holes 500 formed in the base portion 100 and the separation preventer 200. Such an embodiment may provide a lighter implant as compared to an implant without the plurality of through holes. Although not shown in the drawings, in some embodiments, the plurality of through holes 500 may be formed in only the base portion 100. In still other embodiments, the through holes 500 may be formed only in the separation preventer 200. The through holes 500 may have various shapes and different sizes. For example, the through holes 500 may have polygonal shapes such as circles, triangles, and quadrangles. Implant 101 may have through holes with a consistent shapes and sizes, or the implant 101 may have through holes that vary in shape and size in different areas.

In some embodiments, with through holes provided throughout all or substantially all of the implant 101, the implant 101 may be composed of a mesh. In some embodiments, through holes may be positioned in only certain areas of the implant 101.

The through holes 500 may act as fastener holes through which the bone screws 400 (or other bone fasteners) may pass. Also, when the plurality of through holes 500 are provided, each of the bone screws 400 may pass through one of the plurality of through holes and be inserted into the iliac crest 12 at various angles.

Implant Design and Manufacture

To prepare a three-dimensional data model of the implant, first, a three-dimensional image of the pelvis 10 of a recipient is obtained by three-dimensional computerized tomography (CT) scanning of the pelvis. The scan data is transferred to a computer-aided design (CAD) system or other suitable program. Using the scan data, a three-dimensional modeling operation of the base portion 100 is performed. In some embodiments, a shape of the contact surface 110 of the base portion 100 is designed to correspond to a shape of the iliac crest 12 of the pelvis 10.

To determine non-contact portions of the implant, a desired width of the pelvis may be taken into consideration. For example, measurements of a recipient's waist and hip width may be compared to a desired waist-to-hip ratio, and a size and/or shape of the implant may be determined to achieve the desired waist-to-hip ratio.

The three-dimensional data model of the separation preventer may be formed by extending at least a part of a contact surface edge in a curved direction around the imaged iliac crest 12. The one or more fastener holes are created in the three-dimensional model within the base portion 100 and/or the separation preventer according to a programmed algorithm or directly by a user.

Once designed, the implant may be manufactured using a three-dimensional printer in some embodiments. Other methods of manufacturing the implant based on the three-dimensional model may be used.

In situations where a three-dimensional image of the recipient's pelvis is not used, a model of the implant may be created based on data from three-dimensional images of prior recipients, such as average size, typical shapes, etc. In some embodiments, certain data (height, weight, waist size, hip size, etc.) may be measured and correlated to certain implant shapes and/or sizes.

In still other embodiments, an implant may be designed based on trial and error or other methods, and the implants may be manufactured through molding, three-dimensional printing, stamping, or any other suitable method.

Surgery

One method of performing pelvic bone lateral width enlargement surgery using an implant is described below.

According to one embodiment of attaching the implant to a recipient's pelvis, skin at a posterior superior iliac spine 13 is incised. Next, a fixing hole is formed at the iliac crest 12 while examining a corresponding portion through a microscope. The fixing hole is used receive the bone screw that is configured to fix the implant.

The implant 1 is inserted through the incised portion to allow the contact surface 110 to come into close contact with the iliac crest 12. The fastener holes 300 formed in the base portion 100 and/or the separation preventer 200 are aligned with pre-formed fixing holes in the bone, and the bone screws 400 are inserted therein.

In some embodiments, no fixing hole is formed prior to the insertion of the implant into the body. For example, the bone screw(s) may be drilled into the iliac crest 12 while the implant 1 is in close contact with the iliac crest 12.

When the operation of fixing the implant 1 to the iliac crest 12 is completed, the incised portion is sutured to complete the pelvic bone enlargement surgery.

As described above, because the implant 1 is manufactured in the shape corresponding to the shape of the iliac crest 12 in some embodiments, the implant 1 may come into close contact with the iliac crest 12 and increase the lateral width of the pelvis 10 to have a specified proportion relative to the body of the recipient.

In some embodiments, the implant 1 is inserted through the posterior superior iliac spine 13 through a minimal incision and is fixed to the iliac crest 12. As such, there is almost no scarring and limited bleeding due to a small incision so that rapid recovery and resumption of daily life is possible.

According to some embodiments, using the implants and methods disclosed herein for cosmetic surgery on a pelvic bone may decrease the operation time and the recovery period as compared to general autologous fat transplantation methods, and may prevent common side effects of transplanting autologous fat.

Additionally, because implants according to the embodiments disclosed herein may be more stable than transplanted autologous fat, and may be manufactured in various sizes and shape, including personalized sizes and shapes, the implants may meet various needs of recipients. Further, implants according to some embodiments of the present disclosure have little to no risk of being melted and partially dissipated or conglutinated to tissue.

According to some embodiments, an implant may include a cover portion to provide a shape and feel to the implant. For example, in some embodiments, a silicone cover may be attached to the implant and cover a portion of the implant. The silicone cover may be shaped to provide a smoothly curved look to the implant so that when attached to the pelvic bone, the shape of the pelvis and hips look natural. The silicone cover also may provide a more natural feel as compared to the base portion of the implant depending on the materials used. In some embodiments, a solid silicone is used. In some embodiments, a soft silicone may be used. Silicone gel may be used in some embodiments. In other embodiments, a pliable cover made of a material other than silicone may be used.

The silicone may be attached to the base portion of the implant in any suitable manner. For example, the base portion may have thin extensions which pierce the silicone implant. In some embodiments, the silicone cover (or other flexible material cover) may be attached to the base portion with one or more screws or other fasteners that are fastened through the cover and into the base portion. In still other embodiments, the silicone or other cover material may be molded around an extension from the mold. For example, a stainless steel implant may include an extension with a flat plate at the end of the extension. The silicone may be formed over the plate and extension such that the cover abuts the stainless steel portion and is held against the stainless steel implant by the extension and plate.

The silicone may be adhered to the implant with any suitable adhesive. In some embodiments, adhesive may be used in addition to any one or more of the disclosed methods of attachment. In some embodiments, a groove may be formed in the silicone, and the plate may include an insert which fits into the groove.

Figure 12:
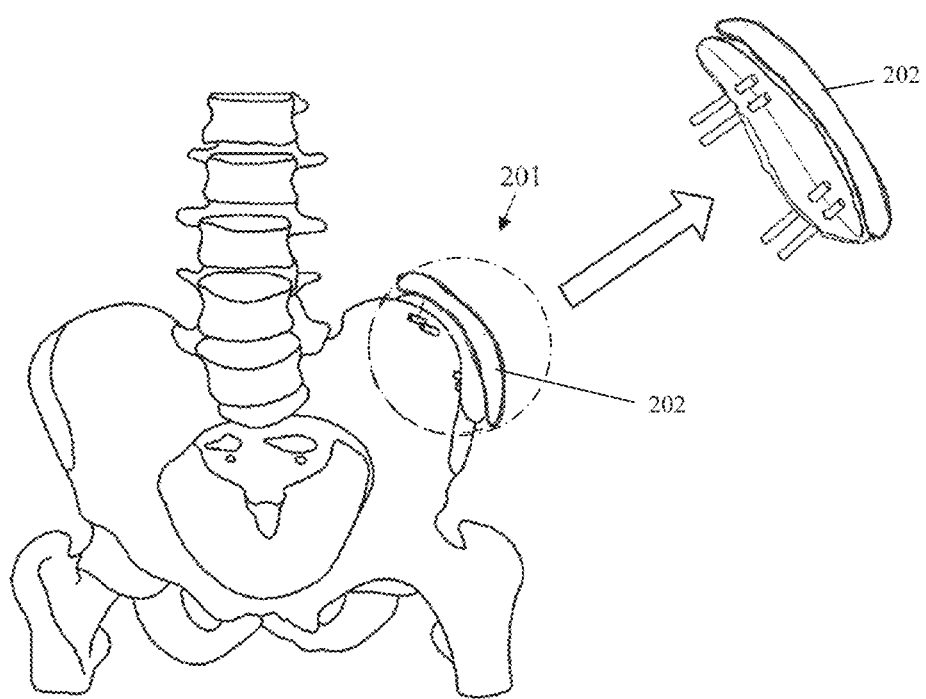
FIG. 12 shows an implant for surgery on a pelvic bone according to another embodiment.

In the embodiment shown in FIG. 12, an implant 201 includes a silicone cover 202 which covers a portion of the outer surface of the base portion. In the illustrated embodiment, bone screws 400 pass through the separation preventer without passing through the silicone cover 202. In some embodiments, the bone screws may pass through the silicone cover as well.

Figure 13:
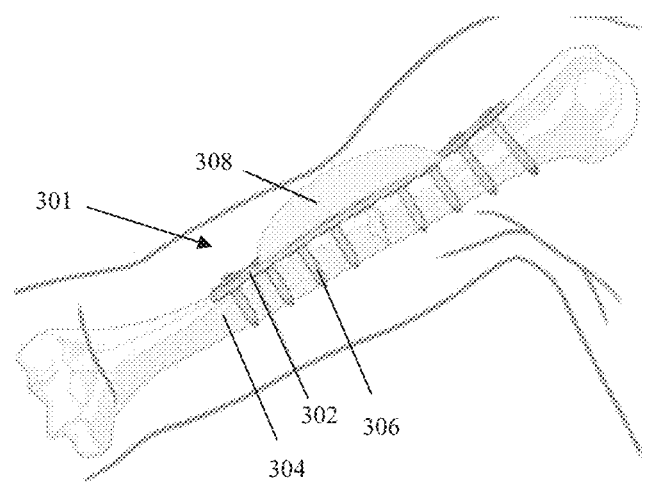
FIG. 13 shows an implant including a plate and silicone implant attached to a humeral bone.

FIG. 13 shows an implant 301 that may be used to change the appearance of a biceps area of a recipient. A plate 302 is attached to a humeral bone 304 via bone fasteners such as bone screws 306. A silicone implant 308, or other type of implant, is attached to the plate 302. In some embodiments the plate 302 and silicone implant 308 are positioned under the biceps muscle. Such an arrangement may provide a more natural looking enhancement of the biceps muscle as compared to silicone implants directly attached onto the muscle. Flexion and extension of the biceps muscle provides a natural motion of the upper arm. When silicone is attached directly the muscle, the silicone does not changes during motion and can look unnatural.

Figure 14:
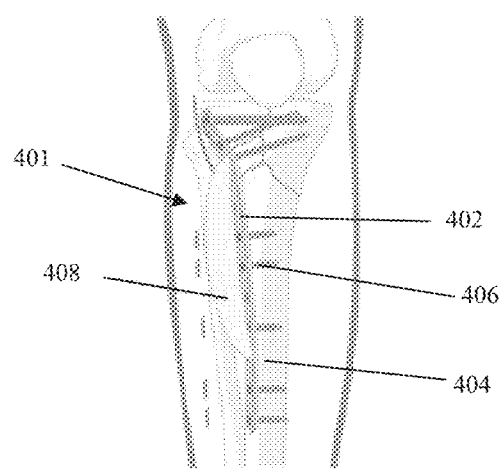
FIG. 14 shows an implant including a plate and silicone implant attached to the anterior of a tibia.

FIG. 14 shows an implant 401 that may be used to change the appearance of a front leg region of a recipient by attachment to the front of a tibia bone 404. The implant may include a plate 402 fixed to the bone via bone screws 406 or other suitable bone fasteners. A silicone implant 408 may be attached to the plate 402.

Figure 15:
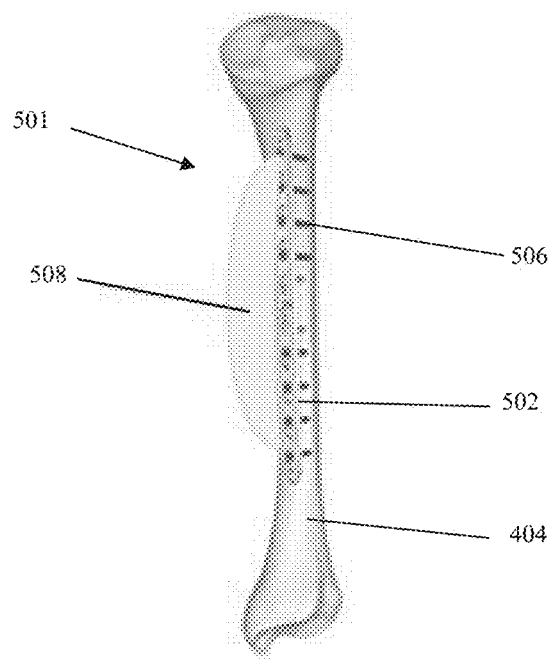
FIG. 15 shows an implant including a plate and silicone implant attached to the posterior of a tibia.

FIG. 15 shows an implant 501 that may be used to change the appearance of a rear leg region of a recipient by attachment to the back of a tibia bone 404. The implant 501 includes a plate 502 fixed to the bone via bone screws 506 or other suitable bone fasteners. A silicone implant 508 may be attached to the plate 502.

Figure 16:
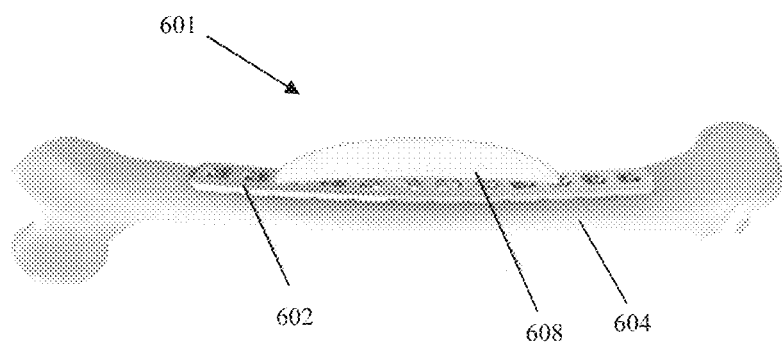
FIG. 16 shows an implant including a plate and silicone implant attached to a femur.

FIG. 16 shows an implant 601 attached to a femur 604. The implant 601 includes a plate 602, such as a metal plate, and a silicone implant 608. One or more bone screws 606 may be used to attach the plate to the bone. In some embodiments, the bone screws may pass through the silicone implant 608.

Figure 17:
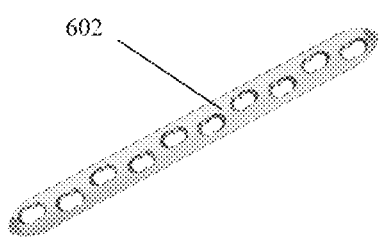
FIG. 17 shows a plate configured to be attached to a bone.

FIG. 17 shows plate 602 prior to attachment of the silicone implant and prior to attachment to the femur. Plates identical or similar to plate 602 may be used to attach a silicone implant to any suitable bone in the human body. In some embodiments, the plate is greater than three millimeters thick. In some embodiments, the plate is greater than five millimeters thick. The plate may have a curvature that corresponds to the curvature of the bone onto which it is to be attached. In some embodiments, the curvature, size, or other attributes of the plate may be determined based on information about the recipient's bone. For example, a femur bone may be imaged as part of determining the shape of the plate to be formed and used.

Even though the terms first, second, etc. may be used for describing various components, the components will not be limited by the terms. The terms are used only for distinguishing one element from others.

When it is stated that one component is connected to another component, it should be understood that the one component may be directly connected to the other component, or that the one component may be indirectly connected to another component via one or more intermediate components.

The terms used herein only to describe the particular embodiments and are not intended limit the present invention. Singular expressions include plural expressions unless otherwise defined.

While the embodiments of the present invention have been described above with reference to the attached drawings, one of ordinary skill in the art should understand that that the present invention can be modified in various detailed forms without departing from the technical concept and essential features of the present invention. For example, those skilled in the art may change a material, a size, and the like of each component according to an application field, or may combine or displace embodiments in forms not clearly disclosed in the embodiments of the present invention. However, such alterations will not deviate from the scope of the present invention. Therefore, it should be understood that the embodiments described above are exemplary in all aspects and are not limitative, and the modified embodiments should be included in the technical concept defined by the claims of the present invention.

What is claimed is:

1. A bio-compatible implant for cosmetic surgery on a pelvic bone to increase an apparent lateral width of a pelvis of a recipient, the implant comprising:

a base portion including:
an outer surface which is configured to extend laterally beyond an outermost lateral region of an iliac crest when the implant is fixed to the iliac crest of the recipient; and
a concave contact surface configured to contact an outer surface contact area of the iliac crest of the recipient,
wherein the outer surface of the implant has a lateral portion which is configured to correspond in shape to a portion of the iliac crest over which the lateral portion lies; and
a separation preventer extending from an edge of the concave contact surface of the base portion and curved so as to be configured for grasping the iliac crest by wrapping around at least a portion of the iliac crest when the concave contact surface is in contact with the outer surface contact area of the iliac crest.

2. A bio-compatible implant as in claim 1, wherein the contact surface has a shape configured to correspond to a shape of the iliac crest in the outer surface contact area.

3. A bio-compatible implant as in claim 1, wherein a contact surface shape is configured to match an outer surface shape of at least a portion of the iliac crest of the recipient.

4. A bio-compatible implant as in claim 1, further comprising a plurality of fastener holes.

5. A bio-compatible implant as in claim 4, further comprising one or more bone fasteners configured to selectively pass through one or more fastener holes among the plurality of fastener holes to attach the implant to the iliac crest.

6. A bio-compatible implant as in claim 1, wherein the implant comprises a titanium alloy.

7. A bio-compatible implant as in claim 1, wherein the implant comprises a stainless steel alloy.

8. A bio-compatible implant as in claim 1, wherein the implant comprises polyethylene.

9. A bio-compatible implant as in claim 1, wherein the implant comprises a bio-ceramic.

10. A method of increasing an apparent lateral width of a human pelvis, the method comprising:
(a) contacting a bio-compatible implant to an iliac crest of a recipient; and
(b) inserting one or more bone fasteners into the iliac crest to fix the implant to the iliac crest in a position in which the implant extends laterally beyond an outermost lateral region of the iliac crest,
wherein the implant comprises:
a base portion including:
an outer surface which is configured to extend laterally beyond the outermost lateral region of the iliac crest when the implant is fixed to the iliac crest of the recipient; and
a concave contact surface configured to contact an outer surface contact area of the iliac crest of the recipient,
wherein the outer surface of the implant has a lateral portion which is configured to correspond in shape to a portion of the iliac crest over which the lateral portion lies; and
a separation preventer extending from an edge of the concave contact surface of the base portion and curved so as to be configured for grasping the iliac crest by wrapping around at least a portion of the iliac crest when the concave contact surface is in contact with the outer surface contact area of the iliac crest.

11. A method as in claim 10, wherein step (b) comprises passing the one or more bone fasteners through one or more fastener holes in the implant.

12. A method as in claim 10, wherein step (b) comprises passing the one or more bone fasteners through one or more fastener holes in a base portion of the implant.

13. A method as in claim 10, wherein step (b) comprises passing the one or more bone fasteners through one or more fastener holes in the separation preventer of the implant, the separation preventer extending from the base portion.

14. A method as in claim 10, further comprising repeating steps (a) and (b) on an opposite iliac crest of the recipient.

15. A method as in claim 10, further comprising forming an implant shape based on an imaging of the recipient's iliac crest.

16. A method of manufacturing an implant for cosmetic surgery on a pelvic bone, the method comprising:
(a) imaging an iliac crest of a recipient; and
(b) forming the implant,
wherein the implant comprises:
a base portion including:
an outer surface which is configured to extend laterally beyond an outermost lateral region of the iliac crest when the implant is fixed to the iliac crest of the recipient; and
a concave contact surface configured to contact an outer surface contact area of the iliac crest of the recipient,
wherein the outer surface of the implant has a lateral portion which is configured to correspond in shape to a portion of the iliac crest over which the lateral portion lies; and
a separation preventer extending from an edge of the concave contact surface of the base portion and curved so as to be configured for grasping the iliac crest by wrapping around at least a portion of the iliac crest when the concave contact surface is in contact with the outer surface contact area of the iliac crest.

17. A method as in claim 16, further comprising:
(c) imaging an opposite iliac crest of the recipient; and
(d) repeating step (b) to form another implant for the opposite iliac crest.

* * * * *

UNITED STATES PATENT AND TRADEMARK OFFICE
CERTIFICATE OF CORRECTION

PATENT NO. : 10,772,728 B2  
APPLICATION NO. : 15/415818  
DATED : September 15, 2020  
INVENTOR(S) : Yougun Won Page 1 of 1

It is certified that error appears in the above-identified patent and that said Letters Patent is hereby corrected as shown below:

On the Title Page

Item (73):  
Assignee: Yougun Kim, Daejeon (KR);  
BOICOEN CO., LTD., Yongin-si, Gyeonggi-do (KR)

Should be:  
Assignee: Yougun Won, Daejeon (KR);  
BIOCOEN CO., LTD., Yongin-si, Gyeonggi-do (KR)

Signed and Sealed this  
Twentieth Day of April, 2021

Drew Hirshfeld  
*Performing the Functions and Duties of the*  
*Under Secretary of Commerce for Intellectual Property and*  
*Director of the United States Patent and Trademark Office*